: 128-24 A   AU 335   EX
5/26/81   OR   4,269,176

United States Patent [19]
Beyer et al.

[11] 4,269,176
[45] May 26, 1981

[54] TREATMENT HEAD FOR ELECTROMEDICAL DIAGNOSTIC OR THERAPEUTIC TREATMENT OF BODY PARTS

[75] Inventors: Johann Beyer, Baiersdorf; Friedrich Strauber, Buckenhof, both of Fed. Rep. of Germany

[73] Assignee: Siemens Aktiengesellschaft, Berlin & Munich, Fed. Rep. of Germany

[21] Appl. No.: 963,583

[22] Filed: Nov. 24, 1978

[30] Foreign Application Priority Data

Dec. 16, 1977 [DE] Fed. Rep. of Germany ... 7738446[U]

[51] Int. Cl.³ .................................................. A61H 1/00
[52] U.S. Cl. ..................... 128/24 A; 128/67; 128/800; 403/223; 403/300
[58] Field of Search ............... 128/24.1, 24.2, 24.5, 128/24 R, 24 A, 44, 49, 52, 41, 800, 801, 795, 796, 32, 67; 403/223, 300, 305

[56] References Cited

U.S. PATENT DOCUMENTS

| | | | |
|---|---|---|---|
| 819,458 | 5/1906 | Richwood | 128/67 |
| 1,998,696 | 4/1935 | Andis | 128/67 |
| 2,280,624 | 4/1942 | Buckley | 128/67 |
| 2,283,285 | 5/1942 | Pohlman | 128/24 A |
| 2,369,881 | 2/1945 | Berns et al. | 128/41 |
| 2,523,547 | 9/1950 | Zerkle | 128/24.5 |
| 2,728,869 | 12/1955 | Pohlman | 128/24 A |
| 3,433,226 | 3/1969 | Boyd | 128/24 A |
| 3,751,082 | 8/1973 | Somerville | 403/223 |
| 4,068,346 | 1/1978 | Binder | 403/300 |

FOREIGN PATENT DOCUMENTS

| | | | |
|---|---|---|---|
| 939046 | 2/1956 | Fed. Rep. of Germany | 128/24 A |
| 951,666 | 10/1956 | Fed. Rep. of Germany | 128/24 A |
| 2307554 | 11/1976 | France | 128/24.5 |
| 490312 | 2/1954 | Italy | 128/24 A |

OTHER PUBLICATIONS

Siemens-Firmenprospekt "Sonostat 633".
Betriebsanleitung, "Sonostat 633"-pp. 9 & 10.

*Primary Examiner*—Robert W. Michell
*Assistant Examiner*—Arthur S. Rose
*Attorney, Agent, or Firm*—Hill, Van Santen, Steadman, Chiara & Simpson

[57] ABSTRACT

In an exemplary treatment head with a first treatment surface where a different treatment surface can be preconnected by means of an adapter piece, the adapter piece can be clipped or pinched onto the first treatment surface by means of a clip or pinch part to shift operation from the first to the second treatment surface. Thereby, the change from first to second treatment surface is rendered possible without extensive additional technical expense.

9 Claims, 3 Drawing Figures

TREATMENT HEAD FOR ELECTROMEDICAL DIAGNOSTIC OR THERAPEUTIC TREATMENT OF BODY PARTS

BACKGROUND OF THE INVENTION

The invention relates to a treatment head for electromedical diagnostic or therapeutic treatment of body parts, particularly with ultrasonic and/or stimulation current, with a first treatment surface, to which an adapter piece with a differing second treatment surface is preconnectable.

Treatment heads of this type require different treatment surfaces according to the shape of the body surface to be treated. Thus, for example, one is able to treat relatively flat body parts, as for example, abdomen, back or chest, with a relatively large treatment surface; more strongly curved body contours such as, for example, rounded upper arms or other joint formations of the body extremities, for example, neck, kneecap or finger joints, too, on the other hand, require a smaller treatment surface. Previously, in the transition from a larger to a smaller treatment surface or vice versa, one has been content with furnishing a separate treatment head for each of the necessary treatment surfaces. The profusion of technical accessories was correspondingly large. A possibility for avoiding this disadvantage consists of a single treatment head with a first treatment surface to which a suitable adapter piece with a different, further treatment surface can be screwed. Although the profusion of technical accessories is thereby reduced, the threaded mechanism is nonetheless connected with an increased cost of manufacture and is also rather cumbersome to manipulate.

SUMMARY OF THE INVENTION

The object of the present invention is to design a treatment head to the effect that it can be quickly brought to bear on any and all different treatment surfaces without great cost and with a simple manipulation.

The object is inventively achieved with a treatment head of the type initially cited in that the adapter piece can be clipped or pinched on the first treatment surface by means of a clip or pinch part in accordance with the change from a first to a second treatment surface.

The invention enables the quick change from a first to a second treatment surface or vice versa with a simple manipulation and without an additional technical expense that is excessive. In the improvement of the invention, the adapter piece should exhibit a clip collar for clipping onto the first treatment surface. Thereby, for the sake of practicality, the adapter surface facing the first treatment surface should bear a ridge-like clip collar running around it. For good mounting and for easy clipping of the clip collar onto the adapter piece, the adapter surface facing the first treatment surface should be provided with at least one groove running around it on a shoulder, into which the collar can be snapped by means of a ridge lip that fits it (or that is appropriate thereto). Correspondingly, in further improvement of the invention, the first surface on the treatment head should be provided with counterclip or pinching means for the adapter piece to be clipped or pinched on. In practical development thereby, in the case of a clip collar, the first treatment surface on the treatment head should be provided with a least one groove into which, upon clipping the adapter piece on, the appropriate ridge lip of the collar snaps. It is also advantageous when the clip collar is provided with a finger placement on the collar circumference that can be slipped over the first treatment surface for applying or removing the adapter piece together with the collar.

Further advantages and details of the invention derive from the following description of a sample embodiment on the basis of the accompanying sheet of drawings in conjunction with the subclaims; and other objects, features and advantages will be apparent from this detailed disclosure and from the appended claims.

DETAILED DESCRIPTION

Figure 1:
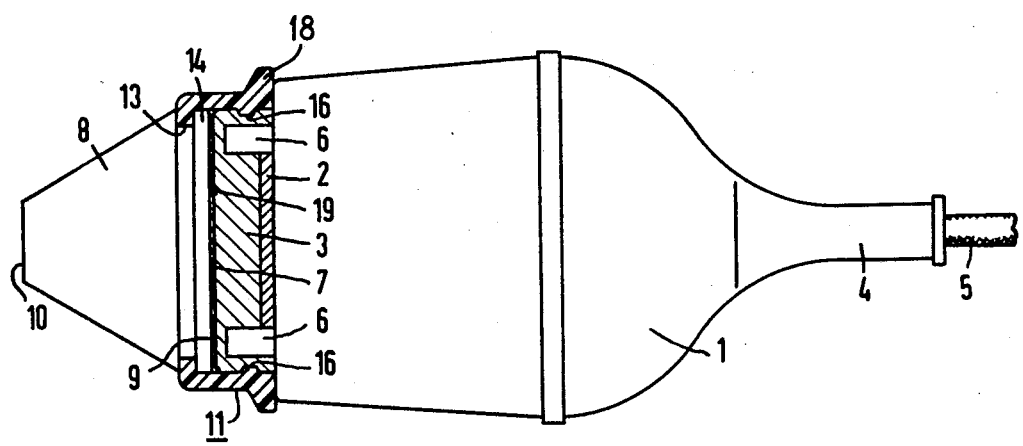
FIG. 1 shows a treatment head specifically for ultrasonic and/or stimulation current treatment with the clipped-on adapter piece, partially in sectional view.

In FIG. 1, the treatment head is designated by reference numeral 1. On its front face, the treatment head 1 bears an ultrasonic transducer 2, which, for example, consists of barium zirconate or barium titanate. Further, a first adapter piece 3, preferably of aluminum, is preconnected to the ultrasonic transducer 2 on the front face of the ultrasonic head 1. In treatment with ultrasonic energy, this first adapter piece 3 has a thickness that amounts to a multiple of the half wavelength ($\lambda/2$) of the ultrasonic waves. For stimulation current treatment instead of ultrasonic radiation or stimulation current treatment together with ultrasonic radiation, the aluminum adapter piece can also simultaneously be the electrode for transmission of the stimulation currents. To this end, it is thus not only the sonic transducer which exhibits an electrical connection to the high frequency excitation oscillator (not illustrated). The adapter piece, too, is then connected via an appropriate electrical circuit with a stimulation current generator. All of the connection circuits are connectable to the corresponding supply installations with a common connection cable 5 via a cable connection 4 of the ultrasonic head.

In FIG. 1, the adapter piece 3 of the treatment head 1 (which is provided with an annular air space 6 for uncoupling the lateral surfaces) exhibits a first treatment surface 7. This first treatment surface 7 of the treatment head 1 exhibits relatively large dimensions. The diameter, for example, lies at circa 42 mm (with a presupposed circular surface). The treatment surface which is thus derived is particularly well suited for adaptation to body parts that are relatively slightly curved.

Should now, however, an adaptation to more strongly curved body parts ensue, then an adapter piece 8 is connected to the ultrasonic head 1 at the front of the first large-surfaced treatment surface 7. This adapter piece 8, which also preferably consists of aluminum, has about the shape of a truncated cone. Accordingly, this truncated cone tapers from a largely joining surface 9, which in the clipped-together state adjoins the first treatment surface 7 of the treatment head, to a second treatment surface 10 with smaller dimensions. When, for example, the coupling surface 9 of the adapter piece 8, in conformation to the treatment surface 7 of the treatment head 1, also has a diameter of circa 42 mm, then the second treatment surface 10 (with a circular form also presupposed) has only a diameter of about 12 mm. It is to be understood, that these dimensions only have the character of being examples; they can be dimensioned differently to correspond with different needs, for example, the use of other types of treatment heads or differently designed adapter pieces, as well.

The clipping of the adapter piece 8 onto the first treatment surface 7 of the treatment head 1 ensues by means of clip collar 11. The clip collar 11 is made out of rubber-like material, particularly silicone rubber or soft plastic. For clipping onto the clipping surface 9 of the adapter piece 8, the collar ring 11 exhibits a circumferential ridge lip 12 which fits into a circular groove 13 on a shoulder 14 of the clipping surface 9 of the adapter piece. Thus, the collar 11 can be snapped into this groove 13 on the adapter piece 8 by means of ridge lip 12. In this particular embodiment, the ridge lip 12 is also additionally provided with an undercut 15, which amounts to circa 30° in the manner illustrated, but which, in different embodiments, can also take in angles of, for example, 45° or more. The undercut guarantees the particularly good fitting of the adapter piece with the surface 9 onto the treatment surface 7 of the ultrasonic head, even in the case of relatively strongly fluctuating production tolerances.

For clipping the adapter piece 8 onto the treatment surface 7 of the treatment head 1 by means of clip collar 11, the treatment surface 7 of the treatment head also exhibits at least one groove 16 on the adapter piece 3, into which groove a corresponding ridge lip 17 of the collar snaps upon clipping the collar on. The groove 16 of the treatment surface 7 and the corresponding ridge lip 17 of the collar 11 are again designed to extend about the entire circumference and to be ring-shaped. But beyond that, though, the clip collar is also provided with a finger engageable placement 18 on the collar circumference that can be slipped over the first treatment surface 7 of the treatment head 1 for applying or removing the adapter piece 8 together with the collar 11. Thereby, according to the embodiment of FIGS. 1 and 3, the finger placement is designed as a cup-edge-shaped circumferential ridge.

Figure 2:
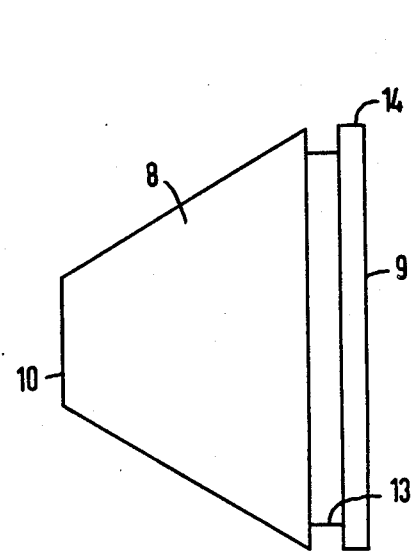
FIG. 2 shows an adapter piece released from the clip collar.
Figure 3:
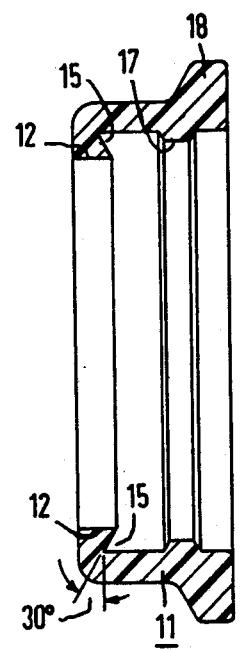
FIG. 3 shows a clip collar for clipping an adapter piece onto the treatment head.

In FIGS. 2 and 3, the adapter piece 8 and collar 11 are again illustrated lying next to each other as unmounted single parts in an exploded projection. It is also worth mentioning that the adapter piece 8 can also exhibit a length that again amounts to a whole number multiple of the half wavelength of the ultrasonic waves in the ultrasonic radiation. But length and surface can also be coordinated with one another in such a manner that, upon preconnection of the adapted piece, essentially the same radiation intensity relationships arise on the second treatment surface as on the first radiation surface of the head 1. Further, for better fitting and ultrasonic transmission, the coupling of the surface 9 of the adapter piece 8 onto the treatment surface 7 of the ultrasonic head 1 should not ensue metal to metal, but, on the contrary, by means of ultrasonic contact paste or water. In FIG. 1, for example, a contact paste (coupling gel) is provided with the reference 19.

It will be apparent that many modifications and variations may be effected without departing from the scope of the novel concepts and teachings of the present invention.

We claim as our invention:

1. A treatment head assembly for electromedical treatment of body parts, comprising an applicator with a first treatment surface (7) having an inner side and an outer side, electromedical treatment means (2, 3) coupled with the inner side of said first treatment surface (7) for activating said first treatment surface (7) for effecting electromedical treatment of a body part when the body part is disposed at the outer side of said first treatment surface (7), said electromedical treatment means (2, 3) comprising an ultrasonic transducer (2) with a first adapter piece (3) interposed between the transducer (2) and said first treatment surface (7), a second adapter piece (8) providing a second treatment surface (10) of different configuration than said first treatment surface (7), and having a base (9) in mating conforming overlying relation to said first treatment surface (7) at the outer side thereof such that the electromedical treatment means (2, 3) is coupled with said second treatment surface (10) of said second adapter piece (8) via said first adapter piece (3) and the first treatment surface (7) and said base (9) for effecting electromedical treatment of a body part disposed at said second treatment surface (10), and said second adapter piece having connected therewith an annular collar (11) having a finger emplacement (18) on the collar circumference and having releasable engagement means releasably engagable with said first adapter piece of said applicator for effecting a positive locking of said second adapter piece (8) to said applicator with the base (9) being held in said mating conforming overlying relation to said first treatment surface (7), means comprising said finger emplacement (18) on said annular collar (11) for accommodating a rapid release of said adapter piece (8) from said first adapter piece (3) of said applicator to expose said first treatment surface (7) at the outer side thereof for direct association with a body part for effecting electromedical treatment thereof, said second adapter piece (8) having an annular groove (13) spaced from the base (9) and defining a shoulder (14), said annular collar (11) having a lip (12) engaged in said annular groove (13) and interlocked with said shoulder (14) to connect said second adapter piece (8) with said annular collar (11), the finger emplacement (18) comprising a circumferential ridge on the annular collar (11), said annular collar (11) being formed of resilient material, said electromedical treatment means (2, 3) including said ultrasonic transducer (2), comprising means for energizing said first treatment surface (7) with ultrasonic energy via said first adapter piece (3), and so as to produce an ultrasonic wavelength λ in said second adapter piece (8), said first adapter piece (3) having a thickness equal to a multiple of the half wavelength of the ultrasonic waves, and said second adapter piece (8) providing a length between its base (9) and said second treatment surface (10) equal substantially to a whole number multiple of the half wavelength (λ/2).

2. A treatment head assembly according to claim 1, with said lip (12) of said annular collar (11) being provided with an undercut (15) on the side confronting said shoulder (14).

3. A treatment head assembly according to claim 2, with said ultrasonic energy being transmitted along an axis of the applicator, the surface of the lip (12) confronting said shoulder (14) normally defining an angle relative to a radial plane with respect to such axis in the range from about 30° to about 45°.

4. A treatment head assembly according to claim 1, with said first adapter piece (3) of said applicator having receiving means (16) for receiving the releasable engagement means of the annular collar (11) in resilient interfitting engagement therewith while accommodating release of said annular collar (11) by means of separating pressure applied at said finger emplacement (18).

5. A treatment head assembly according to claim 4, with said receiving means of said first adapter piece (3) of said applicator comprising at least one groove (16), and said releasable engagement means comprising a lip (17) which snaps into said groove (16).

6. A treatment head assembly according to claim 5, with said groove (16) and said lip (17) being of annular configuration and circumferentially continuous.

7. A treatment head assembly according to claim 1, with said annular collar (11) being formed of silicone rubber.

8. A treatment head assembly according to claim 1, with said annular collar (11) being formed of soft plastic material.

9. A treatment head assembly according to claim 1, with said second adapter piece (8) being formed of a light metal.

* * * * *